(12) United States Patent
Hong et al.

(10) Patent No.: US 10,260,959 B2
(45) Date of Patent: Apr. 16, 2019

(54) MEASUREMENT APPARATUS APPLICABLE TO TWO-DIMENSIONAL RECONSTRUCTION OF GAS IN COMBUSTION FLOW FIELD

(71) Applicant: Space Engineering University, Beijing (CN)

(72) Inventors: Yanji Hong, Beijing (CN); Junling Song, Beijing (CN); Guangyu Wang, Beijing (CN); Wei Rao, Beijing (CN)

(73) Assignee: Space Engineering University, Beijing (CN)

( * ) Notice: Subject to any disclaimer, the term of this patent is extended or adjusted under 35 U.S.C. 154(b) by 0 days.

(21) Appl. No.: 15/959,225

(22) Filed: Apr. 21, 2018

(65) Prior Publication Data

US 2018/0245988 A1 Aug. 30, 2018

Related U.S. Application Data

(63) Continuation of application No. PCT/CN2016/098766, filed on Sep. 12, 2016.

(30) Foreign Application Priority Data

May 26, 2016 (CN) .......................... 2016 1 0356547

(51) Int. Cl.
*G01K 7/12* (2006.01)
*G01K 11/32* (2006.01)
(Continued)

(52) U.S. Cl.
CPC .............. *G01K 7/12* (2013.01); *G01K 11/003* (2013.01); *G01K 11/32* (2013.01); *G01N 21/39* (2013.01);
(Continued)

(58) Field of Classification Search
CPC ........ G01K 7/12; G01K 11/003; G01K 11/32; G01N 21/39
See application file for complete search history.

(56) References Cited

U.S. PATENT DOCUMENTS

| 5,340,216 A | * | 8/1994 | Goldschmidt | ........... G01K 7/12 374/182 |
| 5,798,840 A | | 8/1998 | Beiting | |

(Continued)

FOREIGN PATENT DOCUMENTS

| CN | 103884663 A | 6/2014 |
| CN | 103926200 A | 7/2014 |
| CN | 104483034 A | 4/2015 |

OTHER PUBLICATIONS

Song Junling,Hong Yanji, Wang Guangyu et al. Two-dimensional reconstructions of gas temperature and concentration in combustion based on tunable diode laser absorption spectroscopy. Acta Phys. Sin.,2012,(24):240702.

(Continued)

*Primary Examiner* — Roy M Punnoose
(74) *Attorney, Agent, or Firm* — Wayne & Ken, LLC; Tony Hom

(57) ABSTRACT

The present invention discloses a multi-lightpath and multi-angle measurement apparatus, including an electrically controlled rotary table, electronically controlled translation tables, a laser transmitting/receiving end face, laser couplers, a multipath data acquisition card, a laser controller, a translation controller, an etalon, a laser, detectors, and a computer. The measurement apparatus uses an all-fiber coupling structure, and two ends of the laser transmitting/receiving end face are respectively fixed on two electronically controlled translation tables. Therefore, a maximum area measured by the apparatus is 350 mm×350 mm, and an adjustable minimum translation distance is 1 mm. Bottoms (Continued)

of the translation tables are fixed on the electrically controlled rotary table. Featuring an ingenious design and a compact structure, the whole apparatus is easy to disassemble and easy to operate. The apparatus has high universality, and can implement two-dimensional measurement in a high-temperature combustion flow field.

7 Claims, 3 Drawing Sheets

(51) Int. Cl.
    *G01N 21/85*     (2006.01)
    *G01K 11/00*     (2006.01)
    *G01N 21/39*     (2006.01)
    *G01N 21/47*     (2006.01)
    *G01J 3/02*     (2006.01)

(52) U.S. Cl.
    CPC ......... *G01N 21/4795* (2013.01); *G01N 21/85* (2013.01); *G01J 3/0202* (2013.01); *G01N 2021/399* (2013.01); *G01N 2021/8578* (2013.01); *G01N 2201/066* (2013.01)

(56) References Cited

U.S. PATENT DOCUMENTS

| | | | | |
|---|---|---|---|---|
| 5,813,767 | A * | 9/1998 | Calabro' | F23N 5/082 |
| | | | | 250/345 |
| 6,640,199 | B1 * | 10/2003 | Goldstein | G01K 11/30 |
| | | | | 374/E11.014 |
| 8,544,279 | B2 * | 10/2013 | Sappey | F01D 21/003 |
| | | | | 431/75 |
| 8,786,856 | B2 * | 7/2014 | Estes | F23M 5/08 |
| | | | | 122/510 |
| 8,786,857 | B2 * | 7/2014 | Masterson | F02C 7/00 |
| | | | | 356/437 |
| 9,366,621 | B2 * | 6/2016 | Howell | G01N 21/39 |
| 2008/0289342 | A1 * | 11/2008 | Sappey | F01D 21/003 |
| | | | | 60/793 |
| 2009/0207413 | A1 * | 8/2009 | Carpenter | G01N 21/31 |
| | | | | 356/437 |
| 2011/0045420 | A1 * | 2/2011 | Tanca | F23N 5/003 |
| | | | | 431/12 |

OTHER PUBLICATIONS

Hong Yanji,Song junling,Wang Guangyu,Liu zhaoran.Review on the research of non-uniform combustion field measurement using laser absorption spectroscopy technique. Acta Aeronauticaet Astronutica Sinca,2015,36(3):724-736.

Dai Bin,Ruan Jun,Xu Zhenyu,Li Junsong,Kan Ruifeng,Yao Lu."Measurement of combustor exit temperature field based on tunable diode laser absorption spectroscopy technology". Gas Turbine Experiment and Research. vol. 28,No. 4, Aug. 2015.

E Bryner. "Tunable diode laser absorption technique development for determination of spatially resolved water concentration and temperature" (48th AIAA Aerospace Sciences Meetings including the New Horizons Forum and Aerospace Exposition,AIAA-2010-0299).

Xu Lijun. "Tunable diode laser absorption spectroscopy-based tomography system for on-line monitoring of two-dimensional distribution of temperature and H2O mole fraction". Review of Scientific Instruments.

Li Fei, Yu Xilong, Lin Xin, Zhang Shaohua , Zhang Xinyu ."tunable diode laser absorption spectroscopy,TDLAS".

Li Fei—Tomography TDLAT based on TDLAS ; Chinese Journal of Theoretical and Applied Mechanics vol. 46, No. 1, Jan. 2014.

\* cited by examiner (a)

(b)

(c)

MEASUREMENT APPARATUS APPLICABLE TO TWO-DIMENSIONAL RECONSTRUCTION OF GAS IN COMBUSTION FLOW FIELD

TECHNICAL FIELD

The present invention pertains to the technical field of optical measurement in a combustion flow field, relates to tunable diode laser absorption spectroscopy, and discloses a universal reliable measurement apparatus for two-dimensional reconstruction and development of gas parameters in the combustion flow field.

BACKGROUND

With continuous development of aerospace technologies and increase of national defense construction requirements, more attention is paid to diagnosis and performance evaluation of an engine combustion flow field. A highly efficient combustion flow field measurement means can provide important references for improving combustion efficiency of an engine. In conventional combustion flow field measurement, a contact measurement means, for example, a pneumatic velocity probe, a gas sampling probe, or a thermocouple temperature probe, is mainly used. Contact measurement has disadvantages such as a high maintenance cost, a high failure rate, a low response speed, and inconvenience for carrying and mounting. In addition, an intrusive probe may destruct a measured flow field, and generate a shock wave, causing severe interference to an air flow and affecting measurement accuracy. Therefore, it is necessary to develop an advanced non-contact measurement means.

The tunable diode laser absorption spectroscopy (TDLAS) is an online measurement technology, and has advantages such as a high sensitivity, a high anti-noise capability, and a high environmental adaptability. TDLAS has been extensively applied to diagnosis and research in the combustion flow field and a propulsive flow field in recent years. TDLAS is a line-of-sight measurement technology, and only an average value in a lightpath direction can be obtained. However, in an actual flow field, due to effects of flow mixing, a phase change, a chemical reaction, a heat exchange with wall surfaces, etc., there is an obvious gradient change in a light propagation direction. An average value of a gas parameter in a single path cannot meet a requirement for predicting gas flow characteristics. Therefore, information about spatial distribution of light on a same plane needs to be added to meet a requirement for obtaining two-dimensional distribution of gas. However, because measurement space in the combustion flow field is limited, a higher requirement is imposed on a structural design of a measurement apparatus. In addition, because an experimental apparatus needs to acquire data in dozens of lightpaths, and an amount of data in an experiment is huge, high requirements are imposed on a structure of a measurement apparatus, a measurement method, data transmission, and data processing.

Facing a challenge of two-dimensional reconstruction and measurement of gas parameters in the combustion flow field, persons skilled in the art are greatly concerned about technical issues on how to design the measurement apparatus, improve the measurement method, reduce measurement time, improve measurement accuracy, and implement two-dimensional measurement of gas temperature and component concentration in the combustion flow field.

The following documents and reports relate to designs of a method and an experimental apparatus for two-dimensional reconstruction and measurement of gas parameters in a combustion flow field.

1. "Tunable diode laser absorption technique development for determination of spatially resolved water concentration and temperature" (48th AIAA Aerospace Sciences Meeting including the New Horizons Forum and Aerospace Exposition, AIAA-2010-0299), a dissertation by E Bryner, etc. University of Virginia, U.S.A. A filtered back projection method is used to measure two-dimensional distribution of temperature and component concentration at an outlet of a combustion chamber. Because a complete projection of a measured area is required, during an experiment, data in a total of 1800 lightpaths is acquired from 72 angles in a motion and rotation mode, and data acquisition in the experiment takes nearly one hour.

2. "Application of Diode-Laser-Based Measurements in Hypersonic Flows" (50th AIAA Aerospace Sciences Meeting including the New Horizons Forum and Aerospace Exposition, AIAA-2012-0555), a dissertation by Michael S. Bown, Air Force Research Laboratory, U.S.A. With respect to distribution of temperature and $H_2O$ concentration at an outlet of a HIFiRE-2 combustion chamber, a ground experiment is carried out. At the outlet, six laser lightpaths are installed in a horizontal direction, and eight laser lightpaths are installed in a vertical direction. Two-dimensional distribution of temperature and $H_2O$ concentration at the outlet of the combustion chamber is measured. Because there are projections in two directions only, an obtained result can be used only for qualitative analysis.

3. "Tunable diode laser absorption spectroscopy-based tomography system for on-line monitoring of two-dimensional distributions of temperature and $H_2O$ mole fraction" (Review of Scientific Instruments, issue 1, volume 87, 2016), a dissertation by Xu Lijun, etc., Beihang University. A sector beam projection mode is used, five projection angles are selected, and a cylindrical prism is used for beam splitting. A total of 60 beams are obtained, and a quantity of laser transmitters is reduced effectively. In an experimental apparatus, a cylindrical lens, an anamorphic prism, etc. all need to be fixed on a lab table, and large space is occupied. The experimental apparatus is applicable only to a lab desktop experiment and research. It is difficult to use the experimental apparatus to measure an engine combustion flow field.

4. "Parallel-Beam Tomography Based on TDLAS" (issue 1, volume 46, 2014), a dissertation by Li Fei, etc., Institute of Mechanics, Chinese Academy of Sciences. A rotary measurement apparatus based on six parallel beams is designed. Due to a limitation of hardware conditions in an experiment, a rotation angle is 90°, and therefore, a great error exists in a reconstruction result.

SUMMARY

An objective of the present invention is to design a multi-lightpath and multi-angle measurement apparatus applicable to two-dimensional reconstruction of gas parameters in a combustion flow field. For the first time, the present invention uses a combination of an electrically controlled rotary table and electronically controlled translation tables to implement multi-lightpath and multi-angle two-dimensional measurement of gas parameters in a combustion flow field. In the present invention, the measurement apparatus uses an all-fiber coupling structure to implement use of detectors in an embedded and pluggable manner, save lab space, and improve universality of the apparatus. A data acquisition part in the present invention uses a detector array and a multipath data acquisition design, and can implement synchronous data acquisition in 16 lightpaths. This experimental apparatus may be used to implement two-dimensional measurement of internal flow field parameters in a combustion flow field such as an aero-engine, a ramjet engine, a pulse detonation engine, or a coal furnace, and in particular, implement two-dimensional measurement in dense lightpaths and multiple projection angles in a combustion flow field area with limited measurement space.

The present invention provides a measurement apparatus applicable to two-dimensional reconstruction of gas parameters in a combustion flow field. The apparatus includes an electrically controlled rotary table, an electronically controlled translation table combination, a laser transmitting/receiving end face, a measured area, a laser coupler combination, a laser transmitter, an etalon, a detector array, a laser, a multipath data acquisition card, a translation controller, a laser controller, and a computer.

Laser beams emitted by DFB lasers are combined into one beam by a 1×2 fiber beam splitter, and then the beam is split by a 1×2 fiber beam splitter into two. One beam, after being transmitted by the laser transmitter, passes through the etalon, and then is received by the detector array. The other beam is split by a 1×16 fiber beam splitter into 16 beams, and the 16 beams are transmitted through single-mode fibers to transmitting probes. The laser beam is guided into the measured area. After the laser beam penetrates the measured area and is captured by a large-diameter coupling lens in a receiving probe, the laser beam is transmitted through a multi-mode fiber and enters the detector array. The detector array converts light signals into electrical signals, and transmits the signals to the multipath data acquisition card. The multipath data acquisition card inputs received data into the computer for data processing.

The laser transmitting/receiving end face is a key execution part of the measurement apparatus. Transmitting probes and receiving probes are mounted on each of its four sidewalls, and are connected to the electronically controlled translation tables by the fixing plates. The laser beam is guided into and out of the measured flow field area by using a transmitting probe, a receiving probe, and a fiber. In this way, all-fiber coupling of the measurement apparatus is implemented. The laser transmitting/receiving end face is controlled by using the electronically controlled translation tables and the electrically controlled rotary table. Multi-lightpath and multi-angle two-dimensional planar measurement is implemented in the measured area.

The present invention has the following advantages.

1. Compact structure: An all-fiber coupling design is used. This can reduce sizes of the transmitting probes and the receiving probes, implement use of detectors in an embedded manner, and save measurement space.

2. High accuracy: A beam projection mode based on a combination of motion and rotation is used. Two-dimensional measurement can be implemented in multiple lightpaths and multiple projection angles in the measured combustion flow field, a reconstruction error caused by insufficiency of projected beams is avoided, and measurement accuracy is greatly improved.

3. Convenience for control: Motion of the laser transmitting/receiving end face is controlled by using the electronically controlled translation tables and the electrically controlled rotary table, and automatic measurement is implemented in the measured area. This saves measurement time and improves measurement efficiency. In addition, the all-fiber coupling structure is used. Use in a pluggable manner can be implemented. Operations are simple.

4. High universality: Two-dimensional measurement can be implemented in a measured area within 350 mm×350 mm. A motion range and a rotation angle can be adjusted according to an actual flow field environment. Two-dimensional measurement of combustion flow fields of different types and different sizes can be implemented.

Figure 1:
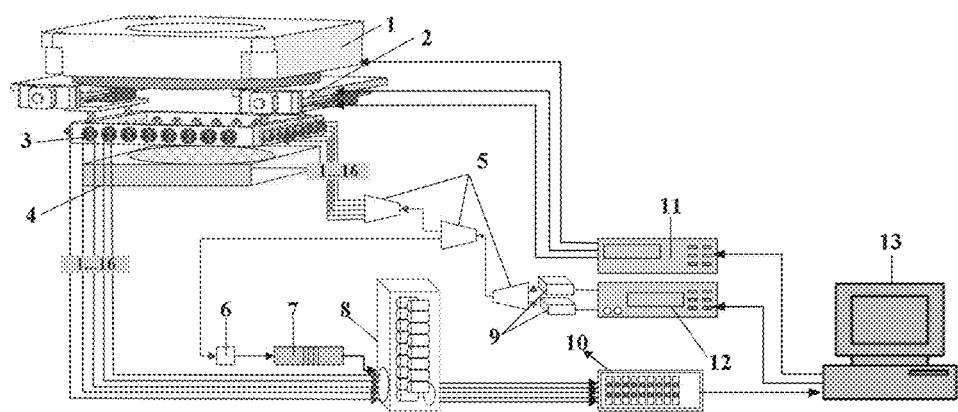
FIG. 1 is a schematic diagram of a measurement apparatus for two-dimensional reconstruction.

In the drawings: 1—electrically controlled rotary table; 2—electronically controlled translation table combination; 3—laser transmitting/receiving end face; 4—measured area; 5—laser coupler combination; 6—laser transmitter; 7—etalon; 8—detector array; 9—laser; 10—multipath data acquisition card; 11—translation controller; 12—laser controller; 13—computer.

DESCRIPTION OF EMBODIMENTS

With reference to the accompanying drawings, the following further describes in detail a measurement apparatus for two-dimensional reconstruction of gas parameters in a combustion flow field.

FIG. 1 provides a schematic diagram of a measurement apparatus for two-dimensional reconstruction. The measurement apparatus includes an electrically controlled rotary table (1), an electronically controlled translation table combination (2), a laser transmitting/receiving end face (3), a measured area (4), a laser coupler combination (5), a laser transmitter (6), an etalon (7), a detector array (8), a laser (9), a multipath data acquisition card (10), a translation controller (11), a laser controller (12), and a computer (13).

Figure 2:
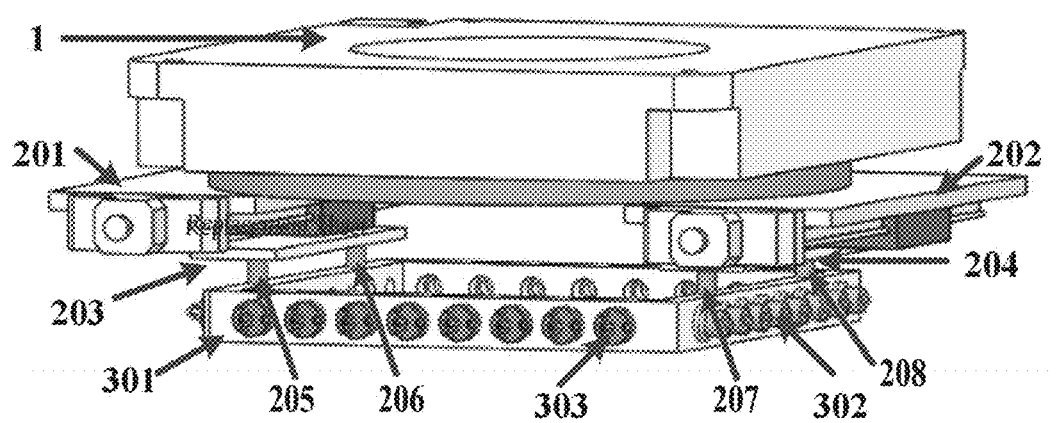
FIG. 2 is a schematic diagram of a rotary table and translation tables.

FIG. 2 provides a schematic diagram of the rotary table and the translation tables, including the electrically controlled rotary table (1), the electronically controlled translation tables (201 and 202), two fixing plates (203 and 204), a fixing frame (301), transmitting probes (302), and receiving probes (303). Bases of the electronically controlled translation tables are fixed on a rotary surface of the electrically controlled rotary table by using four screws. Fixing supports are mounted on top surfaces of the electronically controlled translation tables. Fixing plates are mounted at the other ends of the fixing supports. A bottom side of the fixing frame is connected to the fixing plates respectively.

The fixing frame is made of a stainless steel material and has a rectangular frame structure. An external frame has a length of 280 mm, a width of 275 mm, and a thickness of 28 mm. An internal frame is a square with a length of 250 mm. Eight threaded holes are provided in each of four sidewalls of the fixing frame. The threaded holes are used to mount the transmitting probes and the receiving probes. Diameters of the threaded holes are 24 mm. The electrically controlled rotary table is made of an aluminum alloy material, an outer diameter of a rotary disc is 350 mm, an inner diameter of the rotary disc is 196 mm, a maximum rotation angle is 360°, a maximum rotation speed is 14°/s, and a minimum step angle is 1°. The translation controller is used to implement axial rotation of the electrically controlled rotary table, and further implement automatic rotation of the fixing frame. A maximum travel range of the electronically controlled translation tables is 100 mm, a maximum speed is 20 mm/s, and a minimum motion distance is 1 mm. The translation controller is used to implement synchronous horizontal motion of the electronically controlled translation tables, and further implement horizontal motion of the fixing frame.

The transmitting probe is made of a stainless steel material, and has three angle-adjusting screws. A transmission direction of a laser beam is adjusted by manual fastening or loosening. The transmitting probe has a locking mechanism, and when the transmitting probe is adjusted to a correct position, the transmitting probe can be fixed by the locking mechanism. A focusing lens is provided in the transmitting probe and used to collimate the beam to be transmitted. A sealing washer is provided at two ends of the focusing lens to prevent the lens from being crushed when being locked.

The measurement apparatus uses an all-fiber coupling structure, that is, a fiber for transmission and a fiber for reception. A single-mode fiber is connected to the transmitting probe to guide the laser beam into the measured area. After the laser beam penetrates the measured area and is captured by a large-diameter coupling lens in a receiving probe, the laser beam is transmitted through a multi-mode fiber and enters the detector array. The detector array includes 17 InGaAs detectors. A bandwidth is 4 MHz. A diameter of a photosensitive surface is 3 mm. A detected wavelength range is 800 nm to 1700 nm. Measurement of an absorption spectrum of $H_2O$ in a near-infrared band is implemented.

When the apparatus of the present invention works in a combustion environment, a working process of the apparatus is as follows: First, laser beams emitted by two DFB lasers are combined into one beam by a 1×2 and 50/50 fiber beam splitter, and then the beam is split by a 1×2 and 90/10 fiber beam splitter into two. One beam, after being transmitted by the laser transmitter, passes through the etalon, and then is received by the detector array. The other beam is split by a 1×16 fiber beam splitter into 16 beams, and the 16 beams are transmitted through single-mode fibers to the transmitting probes. The laser beam is guided into the measured area. After the laser beam penetrates the measured area and is captured by a large-diameter coupling lens in a receiving probe, the laser beam is transmitted through a multi-mode fiber and enters the detector array. The detector array converts light signals into electrical signals, and transmits the signals to the multipath data acquisition card. The multipath data acquisition card inputs received data into the computer for data processing. By controlling rotation of the electrically controlled rotary table, the measurement apparatus measures the measured area in different projection angles. By controlling horizontal motion of the electronically controlled translation tables, the measurement apparatus measures different quantities of beams projected in the measured area.

Figure 3:
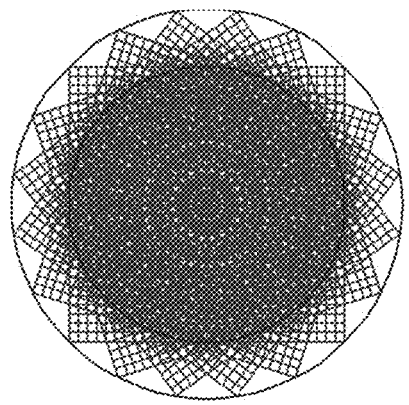
FIG. 3 shows a result of two-dimensional reconstruction and measurement of temperature.
Figure 3:
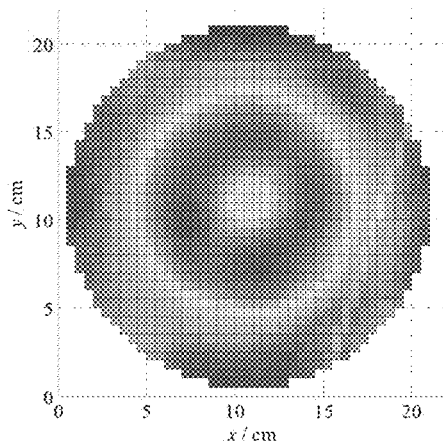
Figure 3:
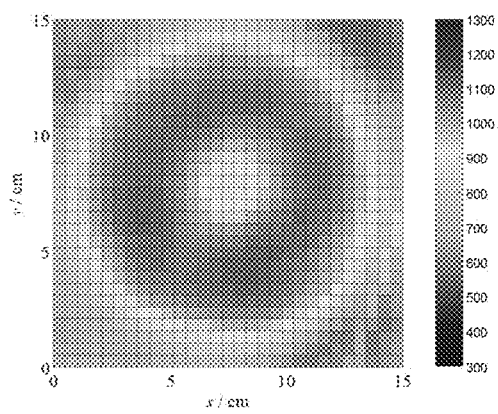

FIG. 3 provides a result of two-dimensional reconstruction and measurement of temperature. FIG. 3(a) is a distribution diagram of beams in 10 projection angles. FIG. 3(b) is a temperature measurement result in the measured area. FIG. 3(c) is a temperature measurement result in a 150 mm×150 mm furnace surface area. The projection angles are evenly distributed in a range of 180°. A resolution of measurement space is 5 mm×5 mm. A reconstructed area is a circular area that uses a furnace surface center as a center and has a radius of 220 mm, including a furnace surface and a nearby indoor temperature area. A height from a measured cross-section to the furnace surface is 5 mm. A measurement result indicates that the apparatus of the present invention can be used to implement two-dimensional reconstruction and measurement of gas temperature in a combustion flow field in multiple lightpaths and multiple angles.

The whole apparatus of the present invention can be used to measure the gas temperature and component concentration in the combustion flow field. Featuring an ingenious design and a compact structure, the apparatus of the present invention is easy to disassemble and easy to operate. The apparatus of the present invention has high universality, and is applicable to two-dimensional measurement of temperature and concentration in a combustion flow field in which temperature is within 1500 K and a measured area is in a range of 350 mm×350 mm.

What is claimed is:

1. A measurement apparatus, comprising:
    an electrically controlled rotary table, an electronically controlled translation table combination, a laser transmitting/receiving end face, a measured area, a laser coupler combination, a laser transmitter, an etalon, a detector array, a laser, a multipath data acquisition card, a translation controller, a laser controller, and a computer;
    wherein the electronically controlled translation table combination comprises two electronically controlled translation tables, two fixing plates, and four fixing supports;
    a top of the electronically controlled translation tables are fixed on a rotary surface of the electrically controlled rotary table by screws; the four fixing supports are mounted on a bottom of the electronically controlled translation tables through the two fixing plates; the laser transmitting/receiving end face (3) comprises a fixing frame (301), 16 transmitting probes (302), and 16 receiving probes (303); eight circular holes are provided in each of four sidewalls of the fixing frame for mounting the 16 transmitting probes and the 16 receiving probes; a top side of the fixing frame is connected to the two fixing plates respectively;
    the laser coupler combination comprises 1×2 fiber beam splitters and a 1×16 fiber beam splitter; the laser comprises distributed feedback laser (DFB lasers) with different center wavelengths; laser beams emitted by the DFB lasers are combined into one beam by the 1×2 fiber beam splitter, and then the beam is split by the 1×2 fiber beam splitter into two, where one beam is split by the 1×16 fiber beam splitter into 16 beams, and the 16 beams are transmitted through fibers to the transmitting probes, and the other beam obtained by splitting by the 1×2 fiber beam splitter is transmitted through a single-mode fiber to the laser transmitter; the etalon receives free light transmitted by the laser transmitter; the detector array comprises 17 InGaAs detectors; the detector array receives light signals transferred by the etalon and the receiving probes through fibers; the detector array converts the light signals into electrical signals, and inputs the signals into the multipath data acquisition card by using a coaxial cable; the multipath data acquisition card inputs received data into the computer; the translation controller is connected to the electrically controlled rotary table, and the electronically controlled translation tables; and the laser controller is connected to the DFB lasers.

2. The measurement apparatus of claim 1, wherein the fixing frame is made of a stainless steel material and has a rectangular frame structures; an external frame has a length of 280 mm, a width of 275 mm, and a thickness of 28 mm, and an internal frame is a square with a length of 250 mm;

and eight threaded holes are provided in each of the four sidewalls of the fixing frame, diameters of the threaded holes are 24 mm, and the threaded holes are used to mount the transmitting probes and the receiving probes.

3. The measurement apparatus of claim 1, wherein the transmitting probe is made of a stainless steel material, the transmitting probe has three angle-adjusting screws, a transmission direction of the laser beam is adjusted by manual fastening or loosening, the transmitting probe has a locking mechanism, and when the transmitting probe is adjusted to a correct position, the transmitting probe is fixed by the locking mechanism; and a focusing lens is provided in the transmitting probe and used to collimate the beam to be transmitted, and a sealing washer is provided at two ends of the focusing lens to prevent the lens from being crushed when being locked.

4. The measurement apparatus of claim 1, wherein the measurement apparatus comprises a fiber for transmission and a fiber for reception; a single-mode fiber is connected to the transmitting probe to guide the laser beam into the measured area; after the laser beam penetrates the measured area and is captured by a large-diameter coupling lens in the receiving probe, the laser beam is transmitted through a multi-mode fiber and enters the detector array; a core diameter of a single-mode fiber at a transmitting end is 9 µm; and a core diameter of a multi-mode fiber at a receiving end is 400 µm.

5. The measurement apparatus of claim 1, wherein the electrically controlled rotary table is made of an aluminum alloy material; an outer diameter of a rotary disc is 350 mm, an inner diameter of the rotary disc is 196 mm, a maximum rotation angle is 360°, a maximum rotation speed is 14°/s, and a minimum step angle is 1°; and the translation controller is used to implement horizontal rotation of the electrically controlled rotary table, and further implement automatic rotation of the fixing frame.

6. The measurement apparatus of claim 1, wherein the electronically controlled translation tables have a maximum travel range of 100 mm, a maximum speed of 20 mm/s, and a minimum motion distance of 1 mm; and the translation controller is used to implement synchronous horizontal motion of the electronically controlled translation tables, and further implement horizontal motion of the fixing frame.

7. The measurement apparatus of claim 1, wherein the detector array comprises 17 InGaAs detectors, a bandwidth is 4 MHz, a diameter of a photosensitive surface is 3 mm, a detected wavelength range is 800 nm to 1700 nm.

* * * * *